United States Patent [19]
Harrington et al.

[11] Patent Number: 5,811,556
[45] Date of Patent: Sep. 22, 1998

[54] PREPARATION OF MIBEFRADIL VIA A NAPHTHALENYLACETIC ACID

[75] Inventors: Peter J. Harrington, Louisville; Jim-Wah Wong, Boulder, both of Colo.

[73] Assignee: Roche Colorado Corporation, Boulder, Colo.

[21] Appl. No.: 60,168

[22] Filed: Apr. 14, 1998

Related U.S. Application Data

[60] Provisional application No. 60/046,795 Apr. 30, 1997.

[51] Int. Cl.⁶ .................................................. C07D 235/14
[52] U.S. Cl. .......................................................... 548/309.7
[58] Field of Search .......................................... 548/309.7

[56] References Cited

U.S. PATENT DOCUMENTS

| | | | |
|---|---|---|---|
| 4,680,310 | 7/1987 | Hengartner et al. | 514/539 |
| 4,808,605 | 2/1989 | Branca et al. | 514/394 |
| 5,120,759 | 6/1992 | Hengartner et al. | 514/452 |

OTHER PUBLICATIONS

B.M. Trost et al., "New Synthetic Reactions. Alkylation of Lactam Derivatives", *J. Org. Chem.*, 39(16), 2475–6 (1974).

R.P. Woodbury et al., "Isolation and Reactions of α–Lithio N,N–Dimethylacetamide", *J. Org. Chem.*, 42(10), 1688–90 (1977).

V. Bažant et al., "Properties of Sodium–bis–(2–methoxy-ethoxy)aluminiumhydride. I. Reduction of Some Organic Functional Groups", *Tetrahedron Letters*, 1968, 3303–6.

H.R. Wiltshire et al., "Metabolism of calcium antagonist Ro 40–5967 . . . ", *Xenobiotica*, 22(7), 837–57 (1992).

S. Chandrasekaran et al., "Synthesis of Substituted β–Lactams by Addition of Nitromethane . . . ", *J. Org. Chem.*, 42(24), 3972–4 (1977).

D.B. Bryan et al., "Nuclear Analogues of β–Lactam Antibiotics. 2 . . . ", *J. Am. Chem. Soc.*, 99(7), 2353–5 (1977).

G.J. O'Malley et al., "Tremorgenic Mycotoxins: Synthesis of 6–Demethyloxyfumitremorgin C", *Tetrahedron Letters*, 28(11), 1131–4 (1987).

M. Leplawy et al., "Peptides—XI. Synthesis of Peptides Derived from Alpha–Methylamine", *Tetrahedron*, 11, 39–51 (1960).

*Primary Examiner*—Laura L. Stockton
*Attorney, Agent, or Firm*—Heller Ehrman White & McAuliffe

[57] ABSTRACT

A method of preparing 2-[2-{[3-(1H-benzimidazol-2-yl) propyl]methylamino}ethyl]-6-fluoro-1-isopropyl-1,2,3,4-tetrahydronaphthalen-2-yl methoxyacetate comprises contacting (6-fluoro-2-hydroxy-1-isopropyl-1,2,3,4-tetrahydronaphthalen-2-yl)acetic acid or an activated derivative of (6-fluoro-2-hydroxy-1-isopropyl-1,2,3,4-tetrahydronaphthalen-2-yl)acetic acid with [3-(1H-benzimidazol-2-yl)propyl]methylamine to form N-[3-(1H-benzimidazol-2-yl) propyl]-2-(6-fluoro-2-hydroxy-1-isopropyl-1,2,3,4-tetrahydronaphthalen-2-yl)-N-methylacetamide, reducing this to 2-[2-{[3-(1H-benzimidazol-2-yl)propyl]methylamino}ethyl]-6-fluoro-1-isopropyl-1,2,3,4-tetrahydronaphthalen-2-ol, and treating the 2-[2-{[3-(1H-benzimidazol-2-yl) propyl]-methylamino}ethyl]-6-fluoro-1-isopropyl-1,2,3,4-tetrahydronaphthalen-2-ol with methoxyacetic acid or an activated derivative of methoxyacetic acid. The invention is particularly applicable to the preparation of mibefradil, (1S,2S)-2-[2-{[3-(1H-benzimidazol-2-yl)propyl] methylamino}-ethyl]-6-fluoro-1-isopropyl-1,2,3,4-tetrahydronaphthalen-2-yl methoxyacetate, and its dihydrochloride salt. N-[3-(1H-benzimidazol-2yl)propyl]-2-(6-fluoro-2-hydroxy-1-isopropyl-1,2,3,4-tetrahydronaphthalen-2-yl)-N-methylacetamide is new.

19 Claims, No Drawings

{ 5,811,556 }

PREPARATION OF MIBEFRADIL VIA A NAPHTHALENYLACETIC ACID

CROSS-REFERENCE TO RELATED APPLICATIONS

This application claims the benefit under 35 USC 119(e) of provisional application No. 60/046,795, filed Apr. 30, 1997, which is incorporated herein by reference in its entirety.

The subject matter of this application is related to the subject matter of application Ser. No. 09/060,151 (Attorney Docket No. 22138-1004), entitled "PREPARATION OF MIBEFRADIL VIA AN ACETAMIDE ANION", and of application Ser. No. 09/060,401 (Attorney Docket No. 22138-1006), entitled "PREPARATION OF MIBEFRADIL VIA AN ACETONITRILE ANION", both filed simultaneously with this application. Application Ser. No. 09/060,151 claims the benefit under 35 USC 119(e) of provisional application No. 60/045,151, filed Apr. 30, 1997, and application Ser. No. 09/060,401 claims the benefit under 35 USC 119(e) of provisional application No. 60/045,150, filed Apr. 30, 1997 These applications and other documents referred to elsewhere in the specification of this application are incorporated herein by reference in their entirety.

BACKGROUND OF THE INVENTION

This invention relates to the preparation of mibefradil and its dihydrochloride salt.

U.S. Pat. No. 4,808,605 (to Hoffmann-La Roche) discloses various calcium antagonists including mibefradil, (1S,2S)-2-[2-{[3-(1H-benzimidazol-2-yl)propyl]methylamino}ethyl]-6-fluoro-1-isopropyl-1,2,3,4-tetrahydronaphthalen-2-yl methoxyacetate, the dihydrochloride salt of which is the antihypertensive POSICOR®. The synthesis of mibefradil, as described in that patent, involves the reaction of (1S,2S)-6-fluoro-1-isopropyl-2-[2-(4-toluenesulfonyloxy)ethyl]-1, 2,3,4-tetrahydronaphthalene-2-ol with [3-(1H-benzimidazol-2-yl)propyl]methylamine in the presence of Hunig base (ethyldiisopropylamine) to form (1S,2S)-2-[2-{[3-(1H-benzimidazol-2-yl)-propyl]methylamino}ethyl]-6-fluoro-1-isopropyl-1,2,3,4-tetrahydronaphthalen-2-ol, which is then acylated with methoxyacetyl chloride to form mibefradil.

The (1S,2S)-6-fluoro-1-isopropyl-2-[2-(4-toluenesulfonyloxy) ethyl]-1,2,3,4-tetrahydro-naphthalene-2-ol, as described in U.S. Pat. No. 4,680,310 (also to Hoffmann-La Roche), is prepared by reacting (S)-6-fluoro-1-isopropyl-3,4-dihydro-1H-naphthalen-2-one with tert-butyl bromoacetate in the presence of activated magnesium to form tert-butyl (1S, 2S)-(6-fluoro-2-hydroxy-1-isopropyl-1,2,3,4-tetrahydronaphthalen-2-yl)acetate, which is reduced with lithium aluminum hydride to form (1S,2S)-6-fluoro-2-(2-hydroxyethyl)-1-isopropyl-1,2,3,4-tetrahydro-naphthalen-2-ol, and then reacted with 4-toluenesulfonyl chloride in pyridine to form the (1S,2S)-6-fluoro-1-isopropyl-2-[2-(4-toluenesulfonyloxy) ethyl]-1,2,3,4-tetrahydronaphthalene-2-ol.

It would be of value to have a method for the preparation of mibefradil and mibefradil dihydrochloride that affords the desired compound easily and in reproducible high yield and purity, and is readily adaptable to large scale commercial production.

BRIEF SUMMARY OF THE INVENTION

In a first aspect, this invention provides N-[3-(1H-benzimidazol-2-yl) propyl]-2-(6-fluoro-2-hydroxy-1-isopropyl-1,2,3,4-tetrahydronaphthalen-2-yl)-N-methylacetamide, and in particular its (1S,2S)-enantiomer.

In a second aspect, this invention provides a method of preparing N-[3-(1H-benzimidazol-2-yl) propyl]-2-(6-fluoro-2-hydroxy-1-isopropyl-1,2,3,4-tetrahydronaphthalen-2-yl)-N-methylacetamide, and in particular its (1S,2S)-enantiomer, comprising contacting (6-fluoro-2-hydroxy-1-isopropyl-1,2,3,4-tetrahydronaphthalen-2-yl)acetic acid or an activated derivative of (6-fluoro-2-hydroxy-1-isopropyl-1,2,3,4-tetrahydronaphthalen-2-yl)acetic acid, and in particular its (1S,2S)-enantiomer, with [3-(1H-benzimidazol-2-yl)propyl]methylamine.

In a third aspect, this invention provides a method of preparing 2-[2-{([3-(1H-benzimidazol-2-yl)propyl]methylamino}ethyl]-6-fluoro-1-isopropyl-1,2,3,4-tetrahydronaphthalen-2-ol, and in particular its (1S,2S)-enantiomer, comprising reducing N-[3-(1H-benzimidazol-2-yl)propyl]-2-(6-fluoro-2-hydroxy-1-isopropyl-1,2,3,4-tetrahydro-naphthalen-2-yl)-N-methylacetamide, and in particular its (1S,2S)-enantiomer, especially with a metal hydride.

In a fourth aspect, this invention provides a method of preparing 2-[2-{[3-(1H-benzimidazol-2-yl)propyl]methylamino}ethyl]-6-fluoro-1-isopropyl-1,2,3,4-tetrahydronaphthalen-2-yl methoxyacetate and its acid addition salts, and in particular its (1S,2S)-enantiomer, comprising preparing 2-[2-{[3-(1H-benzimidazol-2-yl)propyl]methylamino}-ethyl]-6-fluoro-1-isopropyl-1,2,3,4-tetrahydronaphthalen-2-ol, and in particular its (1S,2S)-enantiomer, as described above, and contacting the product with methoxyacetic acid or an activated derivative of methoxyacetic acid, optionally followed by formation of an acid addition salt, especially the dihydrochloride salt.

In particular, this invention relates to the preparation of mibefradil, (1S,2S)-2-[2-{[3-(1H-benzimidazol-2-yl)propyl]methylamino}ethyl]-6-fluoro-1-isopropyl-1,2,3,4-tetrahydronaphthalen-2-yl methoxyacetate, and its dihydrochloride salt.

DETAILED DESCRIPTION OF THE INVENTION

While the invention will be generally described with reference to the preparation of mibefradil, it will be apparent to one of ordinary skill in the art that the coupling of (R)-6-fluoro-1-isopropyl-3,4-dihydro-1H-naphthalen-2-one with tert-butyl acetate, hydrolysis, and subsequent reaction with [3-(1H-benzimidazol-2-yl)propyl]methylamine, will result in the preparation of (1R,2R)-N-[3-(1H-benzimidazol-2-yl)propyl]-2-(6-fluoro-2-hydroxy-1-isopropyl-1,2,3,4-tetrahydronaphthalen-2-yl)-N-methylacetamide, which may be used to prepare the (1R, 2R)-enantiomer of U.S. Pat. No. 5,120,759 in the same manner as the (1S,2S)-isomer is used here to prepare mibefradil. Accordingly, unless the context requires otherwise, reference to any compound is to be considered as a reference to individual enantiomers of the compound, and to racemic or non-racemic mixtures thereof The process of this invention may be represented schematically as follows:

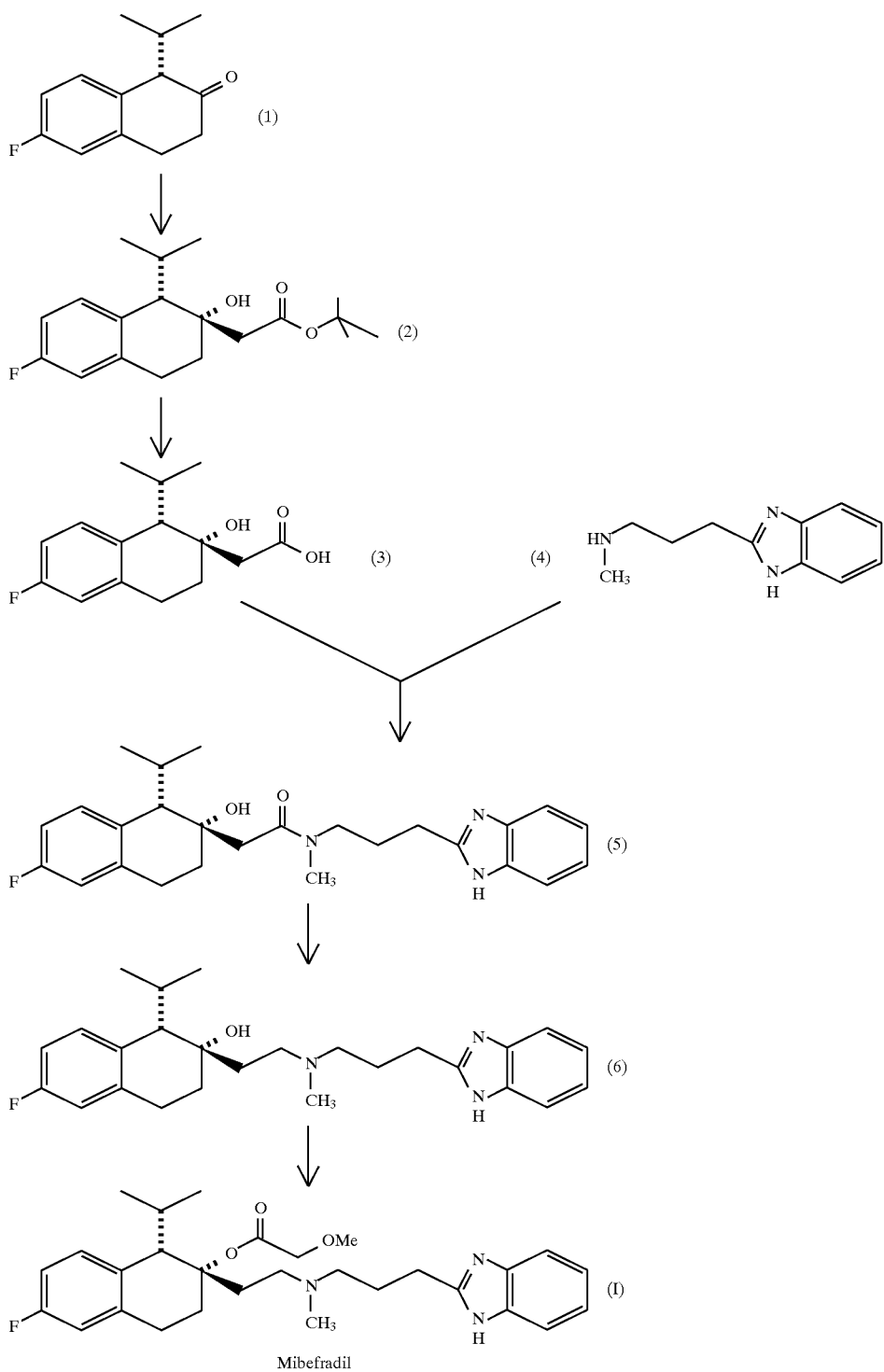

Definitions

An "activated derivative" of (6-fluoro-2-hydroxy-1-isopropyl-1,2,3,4-tetrahydro-naphthalen-2-yl) acetic acid is a derivative that renders the acid more active in the reaction with [3-(1H-benzimidazol-2-yl)propyl]methylamine to form (1S,2S)-N-[3-(1H-benzimidazol-2-yl) propyl]-2-(6-fluoro-2-hydroxy-1-isopropyl-1,2,3,4-tetrahydronaphthalen-2-yl)-N-methylacetamide. Typical such derivatives include the corresponding acyl halides and anhydrides, and a preferred activated derivative is the mixed anhydride of(6-fluoro-2-hydroxy-1-isopropyl-1,2,3,4-tetrahydronaphthalen-2-yl) acetic acid with trimethylacetic acid.

An "activated derivative" of methoxyacetic acid is a derivative that renders the acid more active in the esterification of 2-[2-{[3-(1H-benzimidazol-2-yl)propyl]methylamino}ethyl]-6-fluoro-1-isopropyl-1,2,3,4-tetrahydronaphthalen-2-ol. Typical such derivatives include the methoxyacetyl halides and methoxyacetyl anhydride, and a preferred activated derivative is methoxyacetyl chloride.

An "aprotic polar solvent" includes organic solvents that may be either water-immiscible, such as halogenated hydrocarbons, e.g. methylene chloride, or water-miscible, such as ethers, e.g. tetrahydrofuran and bis(2-methoxyethyl ether), dimethylformamide, N-methylpyrrolidone, dimethylsulfoxide, etc. The solvent may also contain minor proportions of aprotic non-polar solvents such as hydrocarbons, e.g. cyclohexane, toluene, etc., provided that the solvent properties are largely determined by the polar solvent.

Starting Materials

Compounds 1. 6-Fluoro-1-isopropyl-3,4-dihydro-1H-naphthalen-2-one and its (S)-isomer are known, for example, from U.S. Pat. No. 4,680,310, where their preparation from 2-(4-fluorophenyl)-3-methylbutyric acid and its (S)-isomer are disclosed. (R)-6-Fluoro-1-isopropyl-3,4-dihydro-1H-naphthalen-2-one is known, for example, from U.S. Pat. No. 5,120,759, where its preparation from (R)-2-(4-fluorophenyl)-3-methylbutyric acid is disclosed.

Compounds 2. tert-Butyl (6-fluoro-2-hydroxy-1-isopropyl-1,2,3,4-tetrahydronaphthalen-2-yl) acetate and its (1S,2S)-isomer are known, for example, from U.S. Pat. No. 4,680,310. tert-Butyl (1R,2R)-(6-fluoro-2-hydroxy-1-isopropyl-1,2,3,4-tetrahydronaphthalen-2-yl)acetate is known, for example, from U.S. Pat. No. 5,120,759. An alternative synthesis of the tert-butyl ester is shown in the Example.

Compounds 3. (1S,2S)-(6-fluoro-2-hydroxy-1-isopropyl-1,2,3,4-tetrahydronaphthalen-2-yl) acetic acid is known from H.R. Wiltshire et al., *Xenobiotica*, 22(7), 837–857 (1992), as a biliary metabolite of mibefradil in the rat, but no synthesis is given.

Compound 4. [3-(1H-Benzimidazol-2-yl)propyl] methylamine is known, for example, from U.S. Pat. No. 4,808,605, where its preparation from 4-[1-benzyloxy-N-methylformamido]-butyric acid is disclosed.

All other reagents and solvents are readily commercially available, for example from Aldrich Chemical Company or equivalent suppliers.

The Process

In the first step, (S)-6-fluoro-1-isopropyl-3,4-dihydro-1H-naphthalen-2-one, compound 1, is converted to tert-butyl (1S,2S)-(6-fluoro-2-hydroxy-1-isopropyl-1,2,3,4-tetrahydronaphthalen-2-yl) acetate, compound 2, by reaction with the anion of tert-butyl acetate. Typically, tert-butyl acetate is treated with a strong base such as lithium diisopropylamide in an aprotic polar solvent. The tetralone (1) is added to the resulting solution at a reduced temperature, such as at -20° C., and the resulting ester (2) is isolated by neutralization of the reaction mixture, extraction into a water-immiscible organic solvent, and evaporation of the solvent.

In the second step, the ester (2) is hydrolyzed with acid to give (1S,2S)-(6-fluoro-2-hydroxy-1-isopropyl-1,2,3,4-tetrahydronaphthalen-2-yl)acetic acid, compound 3. The hydrolysis may be carried out under conventional conditions for ester hydrolysis, such as with the use of trifluoroacetic acid, but a preferred hydrolysis method uses formic acid as both the solvent and hydrolysis catalyst at room temperature. The acid (3) can be isolated simply by dilution of the formic acid solution with water and cooling, thereby precipitating the acid (3).

Alternative routes to the acid (3) include the base-catalyzed hydrolysis of (1S,2S)-(6-fluoro-2-hydroxy-1-isopropyl-1,2,3,4-tetrahydronaphthalen-2-yl)acetonitrile, which may be prepared from the tetralone (1) by reaction with the anion of acetonitrile; and the base-catalyzed hydrolysis of (1S,2S)-N,N-dimethyl-(6-fluoro-2-hydroxy-1-isopropyl-1,2,3,4-tetrahydronaphthalen-2-yl)acetamide, which may also be prepared from the tetralone (1) by reaction with the anion of N,N-dimethylacetamide. These routes are shown in the Preparation.

In the third step, the acid (3) is reacted with [3-(1H-benzimidazol-2-yl)propyl]-methylamine, compound 4, to form (1S,2S)-N-[3-(1H-benzimidazol-2-yl) propyl]-2-(6-fluoro-2-hydroxy-1-isopropyl-1,2,3,4-tetrahydronaphthalen-2-yl)-N-methylacetamide, compound 5. Typically, the acid (3) is activated by reaction with a trimethylacetyl halide in the presence of an organic base in an organic solvent such as toluene to form the mixed anhydride, which is used as-is in the solution in which it is formed. The mixed anhydride solution is contacted with a solution of the amine (4), forming (1S,2S)-N-[3-(1H-benzimidazol-2-yl) propyl]-2-(6-fluoro-2-hydroxy-1-isopropyl-1,2,3,4-tetrahydronaphthalen-2-yl)-N-methylacetamide, compound 5. A typical recovery procedure for the amide-alcohol (5) involves quenching the reaction mixture with water and extraction of the amide-alcohol (5) into a water-immiscible organic solvent, such as the toluene used as the reaction solvent. The amide-alcohol (5) may be purified by crystallization from an organic solvent such as toluene. The amide-alcohol (5) is new.

In the fourth step, the amide-alcohol (5) is reduced to (1S,2S)-2-[2-{[3-(1H-benzimidazol-2-yl) propyl] methylamino}ethyl]-6-fluoro-1-isopropyl-1,2,3,4-tetrahydronaphthalen-2-ol, compound 6. The reduction is performed with a reducing agent having a high degree of specificity for the reduction of the amide carbonyl group to a methylene group without affecting other portions of the molecule; and suitable reducing agents include the metal hydrides, in particular sodium bis(2-methoxyethoxy) aluminum hydride. Typically, the amide-alcohol (5), in solution in an organic solvent such as toluene, is treated with an excess of the reducing agent (approximately 2.25–3 equivalents when the reducing agent is sodium bis(2-methoxyethoxy)-aluminum hydride), also in solution, by addition of the amide-alcohol (5) to the reducing agent, though the reverse addition is also satisfactory. The crude amide-alcohol (5) solution from the previous step may be used without purification in this step. A typical temperature for the addition is between −5° C. and 10° C.; and the reaction is allowed to continue to completion, typically for approximately 20–24 hours at room temperature or 2–3 hours at 40–45° C. Following completion of the reaction, the reaction mixture is treated in a conventional manner to recover the alcohol (6). A typical recovery procedure for the resulting alcohol (6) involves quenching the reaction mixture with aqueous base and extraction of the alcohol (6) into a water-immiscible organic solvent, such as the toluene used as the reaction solvent.

The alcohol (6) may be isolated if desired by conventional methods, such as by drying the solution containing it with a drying agent such as anhydrous sodium sulfate and evaporation of the solvent. However, it will preferably be isolated as an acid addition salt, such as the dioxalate salt. Preparation and isolation of the dioxalate salt may be performed by conventional methods for the formation of acid addition salts. A presently preferred method, using acetic acid as the solvent, is shown in the Example: the use of acetic acid as solvent is valuable in that it gives the dioxalate salt of the alcohol (6) in especially pure form.

In the fifth step, the alcohol (6) is esterified with methoxyacetic acid or an activated derivative of methoxyacetic acid to form mibefradil, (1S,2S)-2-[2-{[3-(1H-benzimidazol-2-yl)-propyl]methylamino}ethyl]-6-fluoro-1-isopropyl-1,2,3,4-tetrahydronaphthalen-2-yl methoxyacetate, compound I, which is typically isolated as an acid addition salt, especially the dihydrochloride salt. This esterification reaction is known from U.S. Pat. No. 4,808,605, where it is performed with methoxyacetyl chloride in chloroform in the presence of ethyldiisopropylamine; and it will be evident to one of ordinary skill in the art that methoxyacetic acid or other activated derivatives of methoxyacetic acid and other reaction conditions such as are typical in esterification of alcohols may be used. A presently preferred esterification, also using methoxyacetyl chloride, but with toluene as solvent and potassium carbonate sesquihydrate as base, is shown in the Example.

Mibefradil (I) may be isolated as the free base if desired, but will preferably be isolated as an acid addition salt, more preferably as the dihydrochloride salt. The preparation and isolation of mibefradil dihydrochloride may be performed by conventional methods, such as by contacting a solution of mibefradil with a solution of hydrogen chloride in a lower alkanol, followed by crystallization of the salt, as shown in the Example.

The invention is illustrated by the following Preparation and Example.

Preparation: (1S,2S)-(6-Fluoro-2-hydroxy-1-isopropyl-1,2,3,4-tetrahydronaphthalen-2-yl)acetic acid.

Preparation of tert-butyl (1S,2S)-(6-fluoro-2-hydroxy-1-isopropyl-1,2,3,4-tetrahydronaphthalen-2-yl) acetate.

Diisopropylamine, 12.5 mL (9.65 g, 95 mmol) was added by syringe to 20 mL dry tetrahydrofuran at about -20° C. Butyllithium, 38.0 mL of a 2.5 molar solution in hexane (95 mmol), was added dropwise at the same temperature over 40 minutes. After stirring for five minutes, 80 mL dry toluene was added, also at the same temperature, and the solution stirred for a further 1.5 hours. tert-Butyl acetate, 17.6 mL (15.17 g, 131 mmol), was added dropwise at the same temperature over sixteen minutes, the solution stirred for a further 35 minutes, and a solution of 11.22 g (54 mmol) (S)-6-fluoro-1-isopropyl-3,4-dihydro-1H-naphthalen-2-one in 10 mL dry toluene was added dropwise over nineteen minutes. The resulting suspension was warmed to 0° C. over 45 minutes, then stirred at that temperature for a further 45 minutes. The solution was poured over a mixture of 60 g ice, 68 mL water, and 28 mL 12 molar hydrochloric acid, ensuring that the temperature did not exceed 10° C. After stirring for fifteen minutes, the phases were separated, and the aqueous layer (which had a pH of 0) was extracted with 50 mL toluene. The combined organic phases were washed with 50 mL saturated aqueous sodium bicarbonate, dried over anhydrous magnesium sulfate, filtered, and concentrated under vacuum to give 16.45 g tert-butyl (lS,2S)-(6-fluoro-2-hydroxy-1-isopropyl-1,2,3,4-tetrahydronaphthalen-2-yl) acetate as a pale yellow liquid.

Preparation of (1S,2S)-(6-fluoro-2-hydroxy-1-isopropyl-1,2,3,4-tetrahydronaphthalen-2-yl)acetic acid from its tert-butyl ester.

A mixture of 3.02 g crude tert-butyl (1S,2S)-(6-fluoro-2-hydroxy-1-isopropyl-1,2,3,4-tetrahydronaphthalen-2-yl) acetate and 8 mL 96% formic acid was stirred at 25° C. for four hours. The solution was diluted with 6 mL water; then heated to 75° C and filtered. The filtrate was slowly cooled to 25° C. with stirring. The resulting suspension was cooled to 0° C., stirred for one hour, and suction filtered. The precipitate was washed with 15 mL water, air dried at 25° C. for one hour, then oven dried at 50° C. for 22 hours to give 1.59 g (1S,2S)-(6-fluoro-2-hydroxy-1-isopropyl-1,2,3,4-tetrahydronaphthalen-2-yl)acetic acid as a colorless solid, m.p. 102–103.5° C., $[\alpha]_D^{27} = -78.80°$ (CHCl$_3$).

Preparation of (1S,2S)-(6-fluoro-2-hydroxy-1isopropyl-1,2,3,4-tetrahydronaphthalen-2-yl)acetic acid via (1S, 2S)-(6-fluoro-2-hydroxy-1-isopropyl-1,2,3,4-tetrahydronaphthalen-2-yl)acetonitrile.

(1S,2S)-(6-fluoro-2-hydroxy-1-isopropyl-1,2,3,4-tetrahydronaphthalen-2-yl)acetonitrile and its preparation are disclosed and claimed in Application No. 09/060,401.

A 2.5 molar solution of butyllithium in hexane, 10.8 mL, was added dropwise over 20 minutes through an addition funnel to a solution of 1.4 mL acetonitrile in 10 mL tetrahydrofuran at -78° C. The addition funnel was rinsed with an additional 7 mL tetrahydrofuran; and the solution was stirred at -78° C. for 20 minutes. A solution of 4.99 g (S)-6-fluoro-1-isopropyl-3,4-dihydro-1H-naphthalen-2-one in 10 mL tetrahydrofuran was added dropwise through the addition funnel to the solution at -78° C. over 20 min. The addition funnel was rinsed with an additional 2 mL tetrahydrofuran. The light brown solution was allowed to warm to -10° C. over approximately two hours; and was then quenched with 75 mL 5% aqueous hydrochloric acid. The resulting mixture was transferred to a 500 mL separatory funnel; and the reaction vessel was rinsed with 75 mL isopropyl acetate, which was added to the separatory funnel. The aqueous and organic layers were separated, and the aqueous layer was extracted twice with 75 mL isopropyl acetate. The combined organic layers, containing (1S,2S)-(6-fluoro-2-hydroxy-1-isopropyl-1,2,3,4-tetrahydronaphthalen-2-yl)acetonitrile, were concentrated to approximately 10–15 mL.

From a similar preparation in which the nitrile was extracted into diethyl ether instead of isopropyl acetate, the ether solution was dried over anhydrous magnesium sulfate, and the ether removed on a rotary evaporator to give a brown oil, which dried to a beige solid under vacuum drying. A 2.0 g portion of the crude nitrile was recrystallized from hexane to give 1.52 g of pure (1S,2S)-(6-fluoro-2-hydroxy-1-isopropyl-1,2,3,4-tetrahydronaphthalen-2-yl)acetonitrile as a white solid.

(1S,2S)-(6-Fluoro-2-hydroxy-1-isopropyl-1,2,3,4-tetrahydronaphthalen-2-yl)acetonitrile, 250 mg, was mixed with 1 mL 25% aqueous potassium hydroxide, 2 mL methanol, and 0.3 mL 30% aqueous hydrogen peroxide, and the mixture was stirred at 60–65° C. overnight. The methanol was removed on a rotary evaporator, 3 mL water added, and the solution extracted twice with 5 mL portions of diethyl ether. The ether extracts were dried with magnesium sulfate, and stripped to give 80 mg of the acid (3) as a light yellow oil. The aqueous phase was acidified with concentrated hydrochloric acid, and extracted three times with 5 mL portions of diethyl ether. The ether extracts were dried and stripped to give 170 mg of the acid (3) as a light brown oil which solidified on standing.

Preparation of (1S,2S)-(6-fluoro-2-hydroxy-1-isopropyl-1,2,3,4-tetrahydronaphthalen-2-yl)acetic acid via (1S,2S)-N,N-dimethyl-(6-fluoro-2-hydroxy-1-isopropyl-1,2,3,4-tetrahydronaphthalen--2-yl) acetamide.

Lithium diisopropylamide, 1.3 mL of 0.84 molar solution in tetrahydrofuran, was added to a solution of 0.11 mL N,N-dimethylacetamide in 1 mL tetrahydrofuran at -78° C. The mixture was stirred for fifteen minutes, then allowed to warm to -55° C. A solution of 220 mg (S)-6-fluoro-1-isopropyl-3,4-dihydro-1H-naphthalen-2-one in 1 mL tetrahydrofuran was added at that temperature, then allowed to warm to 0–5° C. with stirring, and stirred for 2.5 hours. The reaction mixture was quenched with 3 mL saturated aqueous ammonium chloride, and extracted three times with 3 mL portions of diethyl ether. The ether extracts were combined, dried with magnesium sulfate, and stripped to give 290 mg (1S,2S)-N,N-dimethyl-(6-fluoro-2-hydroxy-1-isopropyl-1, 2,3,4-tetrahydronaphthalen-2-yl)acetamide as a pale yellow oil.

The crude amide was mixed with 1 mL methanol and 1 mL 50% aqueous potassium hydroxide, and heated to 60–70° C. for two days, by which time most starting material had been consumed. The solution was cooled, and 2 mL water and 2 mL diethyl ether added. The mixture was extracted three times with 3 mL portions of diethyl ether. The ether extracts were dried with magnesium sulfate, and stripped to give 40 mg of the acid (3) as a light yellow oil. The aqueous phase was acidified with concentrated hydrochloric acid, and extracted three times with 4 mL portions of diethyl ether. The ether extracts were dried and stripped to give 210 mg of the acid (3) as a brown oil.

Example:

Mibefradil and mibefradil dihydrochloride.

Preparation of (1S,2S)-N-[3-(1H-benzimidazol-2-yl)propyl]-2-(6-fluoro-2-hydroxy-1-isopropyl-1,2,3,4-tetrahydronaphthalen-2-yl)-N-methylacetamide.

Triethylamine, 20.6 mL (14.93 g, 148 mmol) was added dropwise at −5° C. to 0° C. to a solution of 39.30 g (149 mmol) of (1S,2S)-(6-fluoro-2-hydroxy-1-isopropyl-1,2,3,4-tetrahydro-naphthalen-2-yl) acetic acid in 400 mL toluene. The solution was stirred at that temperature for 10 minutes. Trimethylacetyl chloride, 18.2 mL (17.79 g, 148 mmol) and 10 mL toluene were added; and the suspension was stirred at that temperature for ten minutes, warmed to 25° C. over 35 minutes, stirred at that temperature for 25 minutes, then cooled again to 0° C. [3-(1H-Benzimidazol-2-yl)propyl] methylamine, 27.93 g (148 mmol), and 10 mL dry toluene were added, and the mixture was stirred at -5° C. to 0° C. for ten minutes, then at 25° C. for four hours.

Water, 200 mL, was added, and the layers were separated. The organic layer was washed with 200 mL water, dried over anhydrous magnesium sulfate, filtered, and concentrated on a rotary evaporator at 45° C. to afford 169 g of a toluene solution of (1S,2S)-N-[3-(1H-benzimidazol-2-yl)propyl]-2-(6-fluoro-2-hydroxy-1-isopropyl-1,2,3,4-tetrahydronaphthalen-2-yl)-N-methylacetamide. This solution was washed three times with 100 mL 2.5 molar aqueous sodium hydroxide, once with 50 mL brine, and once with 100 mL water. Water or toluene were added as needed to break emulsions during these washes. The organic layer was dried over anhydrous magnesium sulfate, filtered, and then distilled to reduce the volume and remove residual water. The solution was slowly cooled, with stirring, and a seed crystal was added. After stirring at 25° C. for several hours, the precipitate was suction filtered, washed with 75 mL toluene, then dried in vacuo to give 52.93 g (1S,2S)-N-[3-(1H-benzimidazol-2-yl) propyl]-2-(6-fluoro-2-hydroxy-1-isopropyl-1,2,3,4-tetrahydronaphthalen-2-yl)-N-methyl-acetamide as a colorless solid, m.p. 137.5–138.5° C., $[\alpha]_D^{26}$ =16.40° (CHCl$_3$).

Preparation of (1S,2S)-2-[2-{[3-(1H-benzimidazol-2-yl)propyl]methylamino}ethyl]-6-fluoro-1-isopropyl-1,2,3,4-tetrahydronaphthalen-2-ol.

(1S,2S)-N-[3-(1H-Benzimidazol-2-yl)propyl]-2-(6-fluoro-2-hydroxy-1-isopropyl-1,2,3,4-tetrahydronaphthalen-2-yl)-N-methylacetamide, 20.22 g (45.7 mmol), dissolved in 200 mL toluene at 40° C., was added by cannula over 40 minutes at 0–5° C. to a suspension of sodium bis(2-methoxyethoxy)aluminum hydride in toluene, 40 mL (41.44 g suspension, 26.94 g sodium bis(2-methoxyethoxy)aluminum hydride, 133 mmol), and a further 20 mL toluene used to complete the transfer. After completion of the addition, the mixture was stirred at 0° C. for 15 minutes, then at 35–40° C. for three hours.

The mixture was cooled to 25° C. then added carefully to 70 g sodium hydroxide in 140 g ice at less than 10° C. Toluene, 25 mL, was used to complete the transfer. The resulting suspension was warmed to 25° C. over 30 minutes, and the phases were separated. The aqueous phase was. extracted with 25 mL toluene; and the combined toluene phase was washed twice with 50 mL 10% aqueous sodium hydroxide, once with 50 mL water, then once with 50 niL saturated brine. The toluene phase was dried over magnesium sulfate, filtered, and concentrated in vacuo to give 20.61 g (1S,2S)-2-[2-{[3-(lH-benzimidazol-2-yl)propyl] methylamino}ethyl]-6-fluoro-1-isopropyl-1,2,3,4-tetrahydronaphthalen-2-ol as a colorless foam.

Preparation of (1S,2S)-2-[2-{[3-(1H-benzimidazol-2-yl) propyl]methylamino}ethyl]-6-fluoro-1-isopropyl-1,2,3,4-tetrahydronaphthalen-2-ol dioxalate.

Acetic acid, 120 mL, was added to a concentrated toluene solution (15–20 mL) containing approximately 10 g (1S, 2S)-2-[2-{[3-(1H-benzimidazol-2-yl)propyl]methylamino}ethyl]-6-fluoro-1-isopropyl-1,2,3,4-tetrahydronaphthalen-2-ol. An azeotropic mixture of acetic acid and toluene was distilled at ambient pressure until the volume was reduced to about 50 mL. Oxalic acid dihydrate, 5.44 g, was added to the solution, and the solution was stirred at approximately 100° C. for fifteen minutes. The solution was then allowed to cool slowly to 45° C., held at that temperature for two hours, allowed to cool further to 30° C, and held at that temperature for another one hour. A precipitate of (1S,2S)-2-[2-{[3-(lH-benzimidazol-2-yl)propyl]-methylamino}ethyl]-6-fluoro-1-isopropyl-1,2,3,4-tetrahydronaphthalen-2-ol dioxalate formed during this cooling. The mixture was filtered at 30° C., and the warm filtrate was used to rinse residual precipitate onto the filter. The filter cake was washed three times with 10 mL acetic acid at room temperature and dried in a vacuum oven at 55–60° C. under nitrogen flow for eighteen hours to give 9.32 g (1S,2S)-2-[2-{[3-(1H-benimidazol-2-yl)propyl] methylamino}ethyl]-6-fluoro-1-isopropyl-1,2,3,4-tetrahydronaphthalen-2-ol dioxalate as a white solid, containing one molecule of acetic acid of crystallization per molecule of the dioxalate acid addition salt.

Preparation of mibefradil and mibefradil dihydrochloride.

To a 1 L flask was added 41.0 g (actual) (1S,2S)-2-[2-{[3-(1H-benzimidazol-2-yl) propyl]-methylamino}ethyl]-6-fluoro-1-isopropyl-1,2,3,4-tetrahydronaphthalen-2-ol dioxalate, 240 mL water, and 240 mL toluene, with stirring. Potassium hydroxide pellets, 22.4 g, were added, and the mixture heated to 45–50° C. for one hour, with continued stirring. The resulting two-phase mixture was separated using a separatory funnel while still warm. The organic phase was washed with 65 mL water and then vacuum filtered through CELATOM ®(diatomaceous earth filter agent).

To the organic phase was added 39.4 g (4.0 equivalents) potassium carbonate sesquihydrate; then a solution of 21.0 g (17.7 mL, 3.25 equivalents) methoxyacetyl chloride in 33 mL toluene was added over two hours at 25–30° C., and the resulting mixture stirred for an additional 30 minutes at that temperature. Water, 200 mL, was added at room temperature to quench the reaction; and the phases separated using a separatory funnel. The organic phase, containing mibefradil as the free base, was washed with 66 mL water. The washed organic phase was vacuum filtered through a pad of CELATOM®; and most of the toluene removed by distillation at 50° C. and 4 mmHg, leaving a solution of mibefradil in approximately 10 mL toluene. Ethanol, 17.8 mL, was added, and the mixture allowed to cool to room temperature.

To the stirred mixture was added a solution of 4.4 g of hydrogen chloride in 44.6 mL (35.0 g) ethanol at 20° C., and then a further 10.2 mL (8.0 g) ethanol. The resulting mixture was heated to 50° C.; and 1.0 mL water was added, followed by a solution of 3.4 mL water in 332 mL methyl tert-butyl ether over one hour. The mixture was stirred for ten minutes at 50° C., seeded with mibefradil dihydrochloride crystals, then stirred at 50° C. for three hours. A solution of 0.6 mL water in 65 mL methyl tert-butyl ether was added over one hour, and the mixture aged for a further 1.5 hours at 50° C. The mixture was then cooled to 15° C. over two hours and aged at 15° C. for a further hour, and the resulting slurry of mibefradil dihydrochloride was filtered on a Buchner funnel and rinsed with 95 mL dry methyl tert-butyl ether. The product was dried in a vacuum oven at 50° C. to yield mibefradil dihydrochloride as the monohydrate in 95% yield.

While this invention has been described in conjunction with specific embodiments and examples, it will be evident to one of ordinary skill in the art, having regard to this disclosure, that equivalents of the specifically disclosed materials and techniques will also be applicable to this invention; and such equivalents are intended to be included within the following claims.

What is claimed is:

1. N-[3-(1H-Benzimidazol-2-yl)propyl]-2-(6-fluoro-2-hydroxy-1-isopropyl-1,2,3,4-tetrahydronaphthalen-2-yl)-N-methylacetamide, as an individual isomer or as a racemic or non-racemic mixture of isomers.

2. The compound of claim 1 that is (1S,2S)-N-[3-(1H-Benzimidazol-2-yl) propyl]-2-(6-fluoro-2-hydroxy-1-isopropyl-1,2,3,4-tetrahydronaphthalen-2-yl)-N-methylacetamide.

3. A method of preparing N-[3-(1H-benzimidazol-2-yl)propyl]-2-(6-fluoro-2-hydroxy-1-isopropyl-1,2,3,4-tetrahydronaphthalen-2-yl)-N-methylacetamide comprising contacting (6-fluoro-2-hydroxy-1-isopropyl-1,2,3,4-tetrahydronaphthalen-2-yl)acetic acid or an activated derivative of (6-fluoro-2-hydroxy-1-isopropyl-1,2,3,4-tetrahydronaphthalen-2-yl)acetic acid with [3-(1H-benzimidazol-2-yl)propyl]methylamine.

4. The method of claim 3 for preparing (1S,2S)-N-[3-(1H-benzimidazol-2-yl) propyl]-2-(6-fluoro-2-hydroxy-1-isopropyl-1,2,3,4-tetrahydronaphthalen-2-yl)-N-methylacetamide comprising contacting (1S,2S)-(6-fluoro-2-hydroxy-1 -isopropyl-1,2,3,4-tetrahydro-naphthalen-2-yl) acetic acid or an activated derivative of (1S,2S)-(6-fluoro-2-hydroxy-1-isopropyl-1,2,3,4-tetrahydronaphthalen-2-yl) acetic acid with [3-(1H-benzimidazol-2-yl)propyl]methylamine.

5. The method of claim 3 where an activated derivative of the (6-fluoro-2-hydroxy-1-isopropyl-1,2,3,4-tetrahydronaphthalen-2-yl)acetic acid is contacted with the [3-(1H-benzimidazol-2-yl)propyl]methylamine.

6. The method of claim 5 where the activated derivative of (6-fluoro-2-hydroxy-1-isopropyl-1,2,3,4-tetrahydronaphthalen-2-yl)acetic acid is the mixed anhydride of (6-fluoro-2-hydroxy-1-isopropyl-1,2,3,4-tetrahydronaphthalen-2-yl)acetic acid with trimethylacetic acid.

7. The method of claim 6 where the mixed anhydride of (6-fluoro-2-hydroxy-1-isopropyl-1,2,3,4-tetrahydronaphthalen-2-yl)acetic acid with trimethylacetic acid is formed by the reaction of (6-fluoro-2-hydroxy-1-isopropyl-1,2,3,4-tetrahydronaphthalen-2-yl)acetic acid with a trimethylacetyl halide in the presence of an organic base.

8. The method of claim 7 where the trimethylacetyl halide is trimethylacetyl chloride and the organic base is triethylamine.

9. A method of preparing 2-[2-{[3-(1H-benzimidazol-2-yl)propyl]methylamino}ethyl]-6-fluoro-1-isopropyl-1,2,3,4-tetrahydronaphthalen-2-ol comprising treating N-[3-(1H-benzimidazol-2-yl)propyl]-2-(6-fluoro-2-hydroxy-1-isopropyl-1,2,3,4-tetrahydronaphthalen-2-yl)-N-methylacetamide with a reducing agent.

10. The method of claim 9 for preparing (1S,2S)-2-[2-{[3-(1H-benzimidazol-2-yl) propyl]methylamino}ethyl]-6-fluoro-1-isopropyl-1,2,3,4-tetrahydronaphthalen-2-ol comprising treating (1S,2S)-N-[3-(1H-benzimidazol-2-yl)propyl]-2-(6-fluoro-2-hydroxy-1-isopropyl-1,2,3,4-tetrahydronaphthalen-2-yl)-N-methylacetamide with a reducing agent.

11. The method of claim 9 where the reducing agent is a metal hydride.

12. The method of claim 11 where the reducing agent is sodium bis(2-methoxyethoxy)-aluminum hydride.

13. The method of claim 9 further including the step of contacting the thus-formed 2-[2-{[3-(1H-benzimidazol-2-yl)propyl]methylamino}ethyl]-6-fluoro-1-isopropyl-1,2,3,4-tetrahydronaphthalen-2-ol with methoxyacetic acid or an activated derivative of methoxyacetic acid to prepare 2-[2-{[3-(1H-benzimidazol-2-yl)propyl]methylamino}ethyl]-6-fluoro-1-isopropyl-1,2,3,4-tetrahydronaphthalen-2-yl methoxyacetate.

14. The method of claim 10 further including the step of contacting the thus-formed (1S,2S)-2-[2-{[3-(1H-benzimidazol-2-yl)propyl]methylamino}ethyl]-6-fluoro-1-isopropyl-1, 2,3,4-tetrahydronaphthalen-2-ol with methoxyacetic acid or an activated derivative of methoxyacetic acid to prepare (1S,2S)-2-[2-{[3-(1H-benzimidazol-2-yl)propyl]methylamino}-ethyl]-6-fluoro-1-isopropyl-1,2,3,4-tetrahydronaphthalen-2-yl methoxyacetate.

15. The method of claim 13 where the methoxyacetic acid or activated derivative of methoxyacetic acid is methoxyacetyl chloride, and the step of contacting occurs in the presence of a base in an aprotic solvent.

16. The method of claim 13 further including the step of forming an acid addition salt of the 2-[2-{[3-(1H-benzimidazol-2-yl)propyl]methylamino}ethyl]-6-fluoro-1-isopropyl-1,2,3,4-tetrahydronaphthalen-2-yl methoxyacetate.

17. The method of claim 16 where the acid addition salt is the dihydrochloride salt.

18. The method of claim 17 where the step of forming the dihydrochloride salt comprises reacting the 2-[2-{[3-(1H-benzimidazol-2-yl)propyl]methylamino}ethyl]-6-fluoro-1-isopropyl-1,2,3,4-tetrahydronaphthalen-2-yl methoxyacetate with a solution of hydrogen chloride in a lower alkanol.

19. The method of claim 18 where the lower alkanol is ethanol.

* * * * *